(12) United States Patent
Gruenbacher et al.

(10) Patent No.: US 6,669,387 B2
(45) Date of Patent: Dec. 30, 2003

(54) DISTRIBUTING SUBSTANCE ONTO A TARGET SURFACE

(75) Inventors: Dana Paul Gruenbacher, Fairfield, OH (US); James Herbert Davis, Monroe, OH (US); Kevin Joe Fields, Irmo, SC (US); Thomas James Manske, Jr., Mason, OH (US); Dean Arthur Zimmerman, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/315,348

(22) Filed: Dec. 10, 2002

(65) Prior Publication Data

US 2003/0086743 A1 May 8, 2003

Related U.S. Application Data (63) Continuation-in-part of application No. 09/969,074, filed on Oct. 2, 2001, now abandoned, which is a continuation of application No. PCT/US00/27970, filed on Oct. 10, 2000, now abandoned, which is a continuation-in-part of application No. 09/415,866, filed on Oct. 8, 1999, now abandoned.

(51) Int. Cl.[7] .................................................. A46B 5/04
(52) U.S. Cl. ..................... 401/7; 15/104.94; 15/227; 401/133; 604/292
(58) Field of Search ................. 401/6, 7, 132, 401/133, 134, 135; 15/104.94, 227; 604/292, 306

(56) References Cited

U.S. PATENT DOCUMENTS

| | | | |
|---|---|---|---|
| 2,790,982 A | * | 5/1957 | Schneider ....................... 401/7 |
| 4,430,013 A | | 2/1984 | Kaufman |
| 4,891,258 A | * | 1/1990 | Fahrenkrug ................. 428/138 |
| 5,058,247 A | | 10/1991 | Thomas et al. |
| 5,090,832 A | | 2/1992 | Rivera et al. |
| 5,498,692 A | | 3/1996 | Noda |
| 5,518,801 A | | 5/1996 | Chappell et al. |

(List continued on next page.)

FOREIGN PATENT DOCUMENTS

| | | |
|---|---|---|
| AU | 15012 92 | 11/1993 |
| CH | 303374 | 11/1954 |
| CH | 477922 | 9/1969 |
| DE | 3127860 | 2/1983 |
| DE | 3905399 | 2/1990 |
| DE | 9314368 | 9/1993 |
| EP | 0 294 189 | 12/1988 |
| FR | 2632511 | 12/1989 |
| GB | 899016 | 6/1962 |
| GB | 924503 | 4/1963 |
| WO | WO 97/38598 | 10/1997 |
| WO | WO 99/41554 | 8/1999 |
| WO | WO 01/26530 | 4/2001 |

OTHER PUBLICATIONS

"The CFTA Cosmetic Ingredient Handbook," 2nd Ed. (1992).

Dreyfuss, et al., "The Measure of Man," Whitney Library of Design, NY (1969).

Primary Examiner—Gregory Huson
Assistant Examiner—Kathleen J. Prunner
(74) Attorney, Agent, or Firm—Peter D. Meyer (57) ABSTRACT

An applicator is provided for distributing a substance onto a target surface. The applicator includes a first side, a second side, and an internal cavity between said first and second sides. The applicator also comprises at least one opening and at least one substantially fluid-impervious barrier layer within the internal cavity adjacent at least one of the sides. The applicator also comprises a first rupturable, product-containing, flexible film reservoir comprising at least one co-extruded film. A product is released to the target surface upon application of pressure to said reservoir.

19 Claims, 2 Drawing Sheets

U.S. PATENT DOCUMENTS

| | | |
|---|---|---|
| 5,571,849 A | 11/1996 | DesMarais |
| 5,593,670 A | 1/1997 | Trinh et al. |
| 5,649,336 A | 7/1997 | Finch et al. |
| 5,650,214 A | 7/1997 | Anderson et al. |
| 5,714,137 A | 2/1998 | Trinh et al. |
| 5,783,544 A | 7/1998 | Trinh et al. |
| 5,939,060 A | 8/1999 | Trinh et al. |
| 5,942,217 A | 8/1999 | Woo et al. |
| 6,096,067 A | 8/2000 | Cramer et al. |
| 6,305,044 B1 | 10/2001 | James et al. |
| 2001/0036803 A1 | 11/2001 | Fisher |

* cited by examiner

DISTRIBUTING SUBSTANCE ONTO A TARGET SURFACE

CROSS-REFERENCE TO RELATED APPLICATIONS

This application is a continuation-in-part of U.S. patent application Ser. No. 09/969,074, filed Oct. 2, 2001 now abandoned, which is a continuation of PCT Application No. PCT/US00/27970, filed Oct. 10, 2000, now abandoned, which is a continuation-in-part of U.S. patent application Ser. No. 09/415,866, filed Oct. 8, 1999, now abandoned.

FIELD OF THE INVENTION

The present invention relates to an applicator for distributing a substance onto a target surface. More particularly, the present invention relates to applicators that can release a substance and distribute the substance upon the surface of a target object, and then remove the substance from the surface of the target object with the applicator.

BACKGROUND OF THE INVENTION

In the art of dispensing, articles have been developed that are coated or impregnated with substances that are utilized when the substance is contacted with a target surface. However, the primary drawback of these articles is that the substance remaining unprotected and is subject to inadvertent contact with other surfaces before the intended use. Inadvertent contact can lead to contamination of the substance, loss of the substance onto surfaces other than the desired target surface, and/or contamination of other surfaces. Moreover, the use of such articles can frequently result in exposure of a user's hand to the substance. At the very least, such a scenario results in product waste and can be aesthetically undesirable. At worst, the user can be excessively exposed to potentially harmful, toxic, or otherwise undesirable substances.

Other past approaches involve dispensing a substance, such as a cleaner or protectant, from a bottle or other closed vessel onto a target surface and then using a sponge, towel, brush, or other implement to distribute the substance on the surface. Such practices are commonplace with surfaces such as glass, countertops, and other kitchen and bathroom surfaces. While such practices are widely accepted, they result in the inefficient use of product and/or contact with the substances involved. Moreover, the implement used may only provide one type of material surface for use in contacting the substance the target surface.

In a typical glass cleaning operation, a cleaning solution is sprayed onto the surface and subsequently wiped off the surface with a paper towel. Here, cleaning solution is wasted due to overspraying. Overspraying is undesirable, because the cleaning solution can be detrimental to some surfaces and may require these additional surfaces to be cleaned. Additionally, the high absorbency paper towel used to spread the cleaning solution on the surface has a difficult time spreading cleaning solution due to this absorption. A partially saturated paper towel makes spreading the cleaning solution easier. This, in turn, makes the low wet strength paper towel weaker. A dry paper towel is then used to buff the glass dry and absorb excess cleaner. Because this approach requires additional cleaning solution and paper towels, consumers have used newspaper quality paper or low absorbency paper towels. However, this approach can be less desirable because special paper towels are required and significant buffing is required to produce the desired end result.

Some art has combined a gelatin capsule with an applicator substrate. In this regard, the user ruptures the gelatin capsule and dispenses all capsule contents simultaneously and totally upon the target surface. However, gelatin capsules require high forces to rupture. Thus, a rupture is generally uncontrollable, allowing fluid to be dispensed at uncontrolled rates and from uncontrolled locations of the gelatin capsule. Gelatin capsules also generally require the contained product to be non-aqueous. This is because an aqueous solution will generally tend to dissolve the material within the gelatinous structure.

Accordingly, it would be desirable to provide an applicator for applying a substance to a target surface that provides a controlled release of the substance by the user during the application process and further reduces the waste and mess produced by currently utilized application methods. It would also be desirable to provide efficacious combinations of a substance and a substrate for a given task.

SUMMARY OF THE INVENTION

The present invention is an applicator for distributing a product onto a target surface. Generally, the applicator has a first side, a second side, and an internal cavity between the first and second sides. The applicator further comprises at least one opening so that the internal cavity is externally accessible. Additionally, the applicator comprises at least one substantially fluid-impervious barrier layer within the internal cavity adjacent to at least one of the sides. Further, the applicator comprises a first rupturable, product-containing, flexible film reservoir comprising at least one coextruded film. The product is released to the target surface upon the application of pressure to the reservoir.

All documents cited are, in relevant part, incorporated herein by reference; the citation of any document is not to be construed as an admission that it is prior art with respect to the present invention.

DETAILED DESCRIPTION OF THE INVENTION

As used herein, the term "applicator" refers to an article for applying a product to a target surface. An applicator can be semi-enclosed, a mitt, a pad, or a wipe. The term "mitt" refers to a covering for the hand having an enclosure that leaves some or all of the fingers partially or wholly unseparated. This can include space for a thumb in the main enclosure or can provide space for a thumb in a separate enclosure. While the term "mitt" has been defined with respect to the human hand, similar structures could be utilized to cover or enclose other elements of human anatomy, such as a foot.

As used herein, the term "dosing" is defined as the controlled release of a material at desired intervals or at a consistent release rate during use.

As used herein, the terms "pouch" or "sachet" are intended to refer to a reservoir made from an extruded, co-extruded, and/or laminations of an extruded or coextruded film that is unwound, folded, and/or sealed to another film, and then bonded to create one or more enclosed compartments for containing a substance.

The term "semi-enclosed applicator" is intended to refer to an applicator device having at least one externally accessible internal cavity for receiving a portion of human anatomy, such as a hand or finger. Exemplary semi-enclosed applicators include gloves, mitts, and finger mitts. Semi-enclosed applicators can also be provided with a strap, plurality of straps, or backlayer that is sealed along a front portion in order to create a tube-shaped opening on two or more ends.

As used herein, the term "substantially absorbent" is defined as a material composed of a majority of absorbent fibers or web substrates.

As used herein, the term "substantially non-absorbent" is defined as a material composed of a majority of non-absorbent fibers or web substrates.

An absorbent fiber for use in the present invention should have a moisture regain of greater than at least about 5% according to ASTM standard test method D2654-89a. A non-absorbent fiber for the present invention should have a moisture regain of less than about 5%. It has been found that a cellulose acetate fiber has a moisture regain of about 6.5% and a polyester fiber has a moisture regain of about 0.4%.

Applicator Construction

Figure 1:
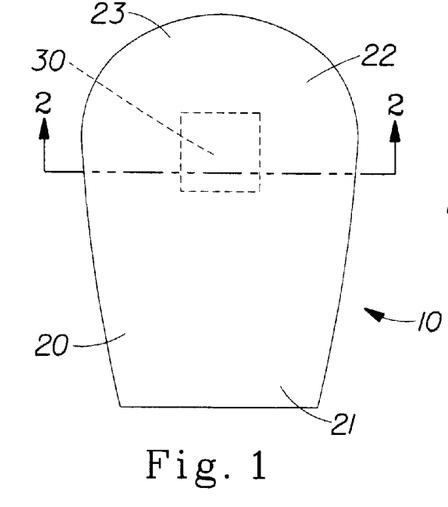
FIG. 1 is a plan view of a preferred embodiment of a semi-enclosed applicator in accordance with the present invention, in the form of a mitt.

FIG. 1 shows an exemplary embodiment of an applicator 10. An applicator 10 generally comprises a body portion 20, cuff portion 21, central portion 22, distal portion 23, and reservoir 30. In general terms, the applicator 10 is provided with an internal cavity that is accessible through an opening in the cuff portion 21 and extends inwardly towards the distal portion 23 that is enclosed.

Figure 2:
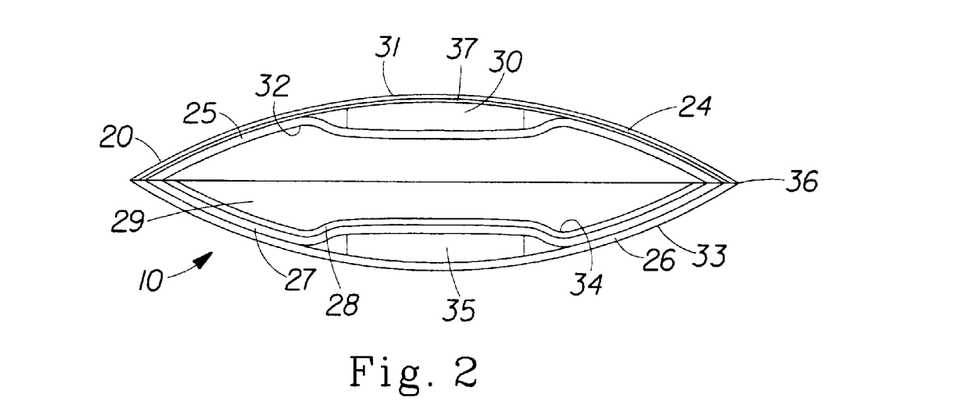
FIG. 2 is a cross-sectional view of the mitt of FIG. 1 taken along line 2—2.

As shown in FIG. 2, applicator 10 has a front outer surface 31, a front inner Surface 32, optional back outer surface 33, and optional back inner surface 34. The front inner surface 32 and back inner surface 34 of applicator 10 define a hollow interior 29 through which a hand can be inserted through an opening in the cuff portion 21. The applicator 10 generally includes a front panel 24 that defines the front outer surface 31, and an optional back panel 26 that defines the back outer surface 33. Front panel 24 and optional back panel 26 are generally connected along their periphery to form a seam 36. Seam 36 can be straight or tapered. For example, seam 36 may be tapered inwardly into the area of the cuff portion 21 to facilitate residence of applicator 10 onto the hand of a user. In addition to, or in place of, tapered seams, elastic material can be added in the cuff portion 21 to keep applicator 10 on the hand of a user. Applicator 10 can then be cut in a desired outline or shape as would be known to one of skill in the art.

It is believed that the applicator 10 of the present invention can be utilized as a conventional cleaning implement for cleaning curved surfaces or surfaces with jagged edges or surfaces having tough-to-reach areas. As a result, the applicator 10 can provide convenience by performing complementary tasks, such as wetting, cleaning, drying, and/or buffing surfaces. Additionally, applicator 10 can be utilized to apply a product to a surface, for example, household surfaces and the skin. A mitt 10 can be stored individually or placed and stacked in containers in a folded or unfolded configuration. Alternatively, an applicator 10 that is provided without optional back panel 26 can be provided with friction enhancing elements on front inner surface 32 to keep the applicator in contact with the hand while in use.

Reservoir

As shown in FIG. 1, reservoir 30 generally contains a product or material that can be dispensed and/or dispersed from reservoir 30 to one or more outer surfaces of the applicator 10 for delivery to a target surface. A reservoir 30 can be of any suitable size, configuration, and composition for the intended product to be dispensed and/or dispersed. Exemplary, but non-limiting products include liquids, gels, lotions, creams, flowable powders, flowable solids, or combinations thereof.

One aspect of the reservoir 30 that is believed to be important to the overall functionality of the semi-enclosed applicator 10 is the ability of a sealed, fully enclosed reservoir 30 to rupture or otherwise dispense a product contained therein when activated by a user and yet resist premature dispensing during manufacture, packaging, and/or shipment.

Referring again to FIG. 2, a reservoir 30 can be located at least partially outside of the applicator 10. The ability of the reservoir 30 to survive intact until the point of use can preserve the quality and quantity of the product. In addition, external accessibility to a reservoir 30 can also facilitate the provision of crimping devices, folding, and/or other methods of protecting the reservoir 30 against premature dispensing. Alternatively, the reservoir 30 can also be provided as a separate article that is inserted into the applicator 10. For example, the reservoir 30 can be inserted inside the front panel 24 or the optional back panel 26 of the applicator 10 or can be inserted into one or more pockets provided between the front outer surface 31 and the front inner surface 32 that are designed to receive the reservoir 30. This can allow the user to replace reservoirs 30 as needed. This can also provide for the re-use of applicator 10 if applicator 10 has retained sufficient absorbency and/or wet strength.

In a preferred embodiment, the reservoir 30 can be designed to burst or rupture and release the material contained within the reservoir 30 at a comparatively low force when desired by the user. This can be accomplished by providing reservoir 30 as a sealed pouch with permanent seals and seals that are frangible (i.e., rupturable). When the pouch is squeezed, the frangible can yield or fail first, since it has a lower peel force than the permanent seals. In an exemplary embodiment, the frangible seal of reservoir 30 will ideally rupture from an applied force ranging from about 0.5 lbs. (2.22N) to about 10.0 lbs. (44.48N), more preferably from about 1.0 lb. (4.48N) to about 7.0 lbs. (31.13N), and most preferably from about 1.0 lb. (4.48N) to about 4.0 lbs. 917.79N) of force.

Stress concentrators in the seal geometry of reservoir 30 that are capable of localizing forces at a particular location can be utilized to optimize the rupture location of reservoir 30. In a preferred embodiment, the stress concentrators can be shaped like a "V", a notch, a half circle, or other shape, depending upon the desired burst force level. These stress concentrators can help control the force required to burst the reservoir 30, as well as the location of where the frangible seal will rupture. Such stress concentrators can thus focus or concentrate external pressure or mechanical forces imposed on reservoir 30 the reservoir 30 and its contents. For example, pressurizing a pouch having a "V"-notch seal 46, such as that shown in FIG. 7, can localize forces first at the apex of the "V" causing that region to rupture first. Such an arrangement can help reduce potential variability in rupture or dispensing forces and the location of reservoir 30 where the rupture occurs. Furthermore, other seal angles and/or geometries of the seal can be used to tailor the force required to rupture reservoir 30 for virtually any particular application.

As shown in FIG. 1, the reservoir 30 can be positioned in the central portion 22 of the applicator 10. In this location, the reservoir 30 can be subjected to sufficient force to rupture the reservoir 30 and dispense the product contained within by making a fist with the user's hand, applying force with an opposite hand, or by pressing the user's palm against a target surface. Locating reservoir 30 in the central portion 22 at applicator 10 can be convenient for applications where it is desired to dispense the product at one time.

Figure 3:
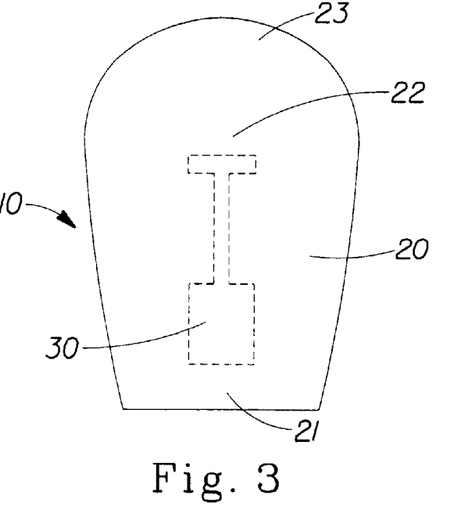
FIG. 3 is another embodiment of a semi-enclosed applicator in accordance with the present invention.

It can also be desired to locate the reservoir 30 in a portion of the applicator 10 that is remote from a location where forces can be applied to reservoir 30 during use. In this case, pressure applied to the applicator 10 during use may not cause premature dispensing or dosing of the product within reservoir 30. In this regard, FIG. 3 depicts an alternative embodiment of a semi-enclosed applicator 10, wherein the reservoir 30 is positioned proximate to the cuff region 21. In this location, reservoir 30 is activated by applying force to the cuff region 21 and would not typically encounter forces during use.

Use of a reservoir 30 to contain a material can allow the applicator 10 to become wet on the desired side only when needed by the user. In some instances, a user may desire to store a single applicator 10 in a remote location. A hermetically sealed reservoir 30 in the applicator 10 would preferably use sufficient barrier materials to allow these individual applicators 10 to have a multiple year shelf life. Separately, the reservoir 30 can be placed on one or both sides of an applicator 10 or in multiple locations on the same side of applicator 10.

Figure 4:
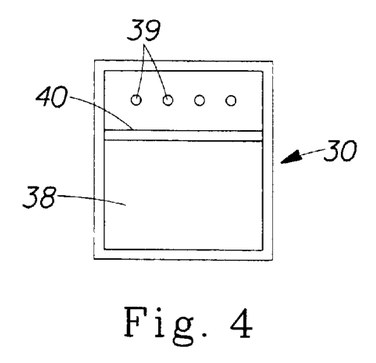
FIG. 4 is a plan view of one embodiment of a rupturable reservoir.

As shown in FIG. 4, one suitable configuration for a rupturable reservoir 30 for use with an applicator 10 generally comprises a chamber 38, a frangible seal 40, and at least one slit, or dispensing aperture, 39. A rupturable reservoir 30 can be made by peripherally joining two similarly sized and shaped pieces of a fluid-impervious material with substantially permanent seals. A dispensing aperture 39 can be formed in at least one portion of one of the pieces of material. Product can then by introduced into reservoir 30 through one of the apertures of dispensing aperture 39, thereby allowing the formation of a frangible seal of limited strength to separate chamber 38 from the dispensing aperture 39. Alternatively, a single piece of fluid-impervious material can be folded upon itself and sealed on three sides or rolled to form a sleeve. The sleeve can then be appropriately sealed as would be known by one of skill in the art to form reservoir 30.

Figure 5:
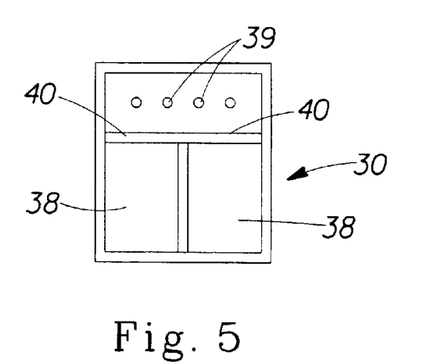
FIG. 5 is a plan view of another embodiment of a rupturable reservoir.

As shown in FIG. 5, another embodiment of a reservoir 30 that can be functionally similar to that shown in FIG. 4 can include a plurality of chambers 38 for containing a material. The plurality of chambers 38 can include materials of the same, similar, or diverse compositions. Further, the chambers 38 can be designed to rupture sequentially or simultaneously, depending on the application of pressure by a user.

Figure 6:
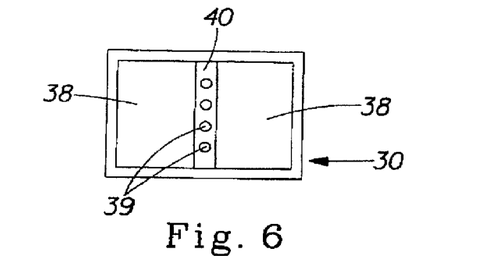
FIG. 6 is a plan view of another embodiment of a rupturable reservoir'

FIG. 6 depicts yet another embodiment of reservoir 30 having a plurality of chambers 38; however, the chambers 38 are individually separated from one another by a rupturable seal 40. As shown, the chambers 38 can be released concurrently to provide the opportunity to mix the materials from respective compartments at the time of dispensing.

Figure 7:
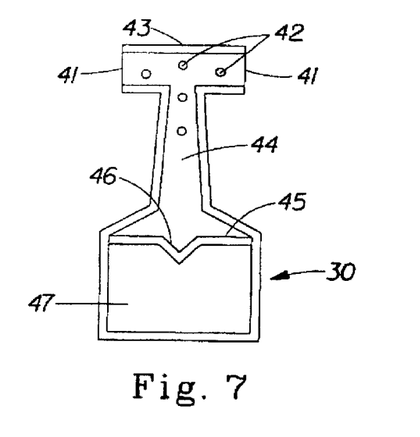
FIG. 7 is a plan view of another embodiment of a rupturable reservoir.

A complex reservoir 30 design, shown in FIG. 7, is provided with a plurality of outlet ducts 41, a plurality of distribution apertures 42, and an elongated channel 44 that separates the chamber 47 from the distal end 43 of the assembly. Fluid flow between the chamber 47 and the channel 44 can be controlled by a frangible or rupturable seal 45 that provides a stress concentration notch 46. The channel 44 can be manufactured from a material and technique that provides self-sealing (i.e., collapses shut to restrict, if not preclude, product flow, except when the chamber is substantially pressurized.) For example, a channel 44 can be formed by making two substantially parallel seals along facing layers of a reservoir 30 where the space between the seals becomes a channel for fluid to move from the reservoir 30 to the distribution apertures 42. This channel can naturally lay flat and stay closed but can become tubular when the reservoir 30 is pressurized and filled with product traveling through the channel 44. Upon the release of pressure, the channel 44 returns to its flattened state, causing a sealing effect to prevent further product delivery. This can allow for selected dosing of a product by a consumer when desired. The dimensions of the channel 44 can be optimized based upon the viscosity of the product being dispensed from the reservoir 30. For example, a reservoir 30 design for dispensing a flowable powder or a relatively thick lotion or cream product preferably has a wider channel 44 than a reservoir 30 designed for dispensing a relatively lower viscosity product. In one preferred embodiment, the channel 44 width is preferably in the range from at least about 0.125 inches (0.32 cm) to at least about 0.5 inches (1.27 cm), more preferably from at least about 0.25 inches (0.64 cm) to allow resealing of the channel 44 while not requiring excessive force on the reservoir 30 to pressurize the channel 44. Resealing the channel can provide for dosing or progressive fluid dispensing. The quantity and size of outlet ducts and/or dispensing apertures 42 can be used to control the dosing and/or dispensing rate of a substance or the force required to dispense a substance, as desired.

Referring again to FIG. 2, another method of dosing can utilize a reservoir 30 combined with a flow restriction layer. A flow restriction layer can be a separate layer in the applicator 10 (i.e., front panel surface 24 or layer 37) or can be an additional layer that is located between layer 37 and the reservoir 30. Non-wovens, wovens, apertured films, thermal formed films, and other materials can be created to have a desired target porosity and fluid flow rate. Without desiring to be bound by theory, it is believed that controlling the mean pore size of openings and the number of openings in a flow restriction layer can determine how fast a fluid or product may be dispensed through the front panel 24 or back panel 26 of applicator 10. The product flow rate can be controlled by incorporating the desired porosity in the front panel 24 or back panel 26 materials or can be accomplished by having a separate layer or layers between the reservoir 30 and the application surface of the applicator 10. An exemplary but non-limiting flow restriction layer can comprise a 100-mesh hydroapertured film made from low density polyethylene. The apertures of this structure are believed to be approximately 100 microns (100 μm) in diameter and can be suitable for controlling the fluid flow rate of creams and lotions. The number and size of the apertures can be adjusted depending upon the viscosity of the product being dispensed and the desired product application rate. An exemplary material for use as a flow restriction layer is a melt-blown non-woven sold by BBA Non-wovens, Inc., Simpsonville, S.C.

The reservoir 30 preferably is formed from a co-extruded film that is laminated to a layer of metallized PET, aluminum foil, $SiO_2$ coated film, or some other high barrier material that can provide an adequate moisture and/or oxygen barrier to allow the product to have a reasonable shelf life. Alternatively, a barrier material, such as ethylene vinyl alcohal (EVOH), nylon, or polyvinylidine chloride (PVDC) can be introduced within the multi-layer co-extruded film, eliminating the need for lamination. Further, a high barrier coating, such as PVDC emulsion coating, can be applied to mono-layer film or co-extruded film to provide the required barrier layer requirements. In one preferred embodiment, the reservoir 30 can have a shelf life in the range from about two years to about three years. Smaller reservoirs with small amounts of a product can require an even higher barrier quality, since the surface area to volume of the product is significantly higher resulting in higher levels of moisture loss due to transport and diffusion.

The reservoir 30 can be made rupturable or frangible by a number of different techniques. Preferably, a reservoir 30 in the form of a pouch is manufactured from a flexible film or substrates provided in a roll form on a vertical or horizontal form/fill/seal machine that has the ability to make different seals on the pouch at different temperatures, pressures, and/or seal times. This can allow one side of a pouch to have a different sealing condition that provides one side with a weaker seal strength.

As would be known to one of skill in the art, a weaker seal strength can be accomplished in a variety of ways. This can include providing two films with different sealant resins, providing a film with the same peelable sealant typically done using a "contaminant" blended into the sealant layer, or providing localized weak areas (e.g., by printing a coating or inserting an incompatible film). A preferred embodiment uses a sealant whose peel strength when sealed to itself shows a suitable peel strength at low temperatures and a higher peel strength at high temperatures.

A suitable sealant material for a frangible seal would be Surlyn® AD8273 manufactured by DuPont® that comprises a blend of polypropylene with an ionomer. Another suitable material is a blend of polybutene-1 (PB-1) with a polyolefin or ethylene copolymer, including, but not limited to, ethylene vinyl acetate (EVA), ethylene methyl acrylate (EMA), ethylene acrylic acid (EAA), ethylene methacrylic acid (EMAA), partially neutralized acid copolymers (ionomers), high density polyethylene (HDPE), linear low density polyethylene (LLDPE), low density polyethylene (LDPE), plastomers, metallocene polyethylene (mPE), polypropylene (PP), or ultra-low density ethylene (ULDPE) copolymers.

The peel strength is strongly affected by the amount of the contaminant (minor phase). In a preferred embodiment, there is at least about 10% of the contaminant present. The blend can contain more than two components. Exemplary but non-limiting potential blends include PB-1/PP/ionomer, HDPE/ionomer/LDPE, EVA/PB/LDPE, or EAA/ionomer/PB/PP. These blends can be made using a twin screw compounder or can be done by adding various resins directly to the film extruder. The blend can provide a contaminant to the base polymer material that can allow the resulting seal to be selectively frangible under certain sealing conditions. For example, at 200° F. (93.3° C.), the sealant layer can deliver a seal force of about 200 to about 400 grams per linear inch (200–400 g/2.54 cm) of seal width and at 300° F. (140.9° C.), the sealant layer can deliver a seal force approximately 3,000 grams per linear inch (3,000 g/2.54 cm) of seal width. This variation in seal strength can allow a pouch to be welded shut in one portion and easily burstable in a second portion by adjusting the seal temperature, the seal time, and/or the seal pressure used when making the pouch seals (e.g., the pouch can be welded along all or a portion of one, two, three, or more sides and easily burstable along a portion of one, two, three, or more sides). A preferable film structure for this type of frangible reservoir could be sealant/tie layer/metallized PET so that the sealant contains PB-1.

Alternative film structures could include a multi-layer co-extrusion that could be the reservoir film by itself or could be laminated to another layer, such as PET, PP, or some other film or substrate. The multi-layer co-extrusion could contain barrier resins, such as, but not limited to, EVOH, PVDC, cyclic olefin copolymers (COC), liquid crystalline polymers (LCP), or polyamides to reduce losses of the contents in the reservoir 30. An exemplary but non-limiting structure could provide a five-layer co-extrusion of LDPE and PB-1/tie layer/EVOH or PVDC/tie layer/HDPE. This structure can be coextruded as a blown or cast film. This high barrier film can provide adequate shelf life for the contents of reservoir 30 and can also prevent transmission losses, evaporation losses, or absorption losses. Optionally, an adequate barrier can be provided from a film having sufficient thickness or by adding barrier coatings to one or more of the layer(s). An exemplary but non-limiting barrier layer could comprise three to six mils (0.076 mm–0.152 mm) of HDPE in combination with another layer that acts as the sealant layer to provide both the frangible and permanent seals. Another example could apply a PVDC barrier coating to a Surlyn®/tie layer/HDPE cast co-extrusion. Other techniques for making a consumer activated rupturable reservoir 30 can include delaminating seals or weak regions in the film structure such as created by embossing, laser scoring, mechanical scoring, or other known methods to one of skill in the art in weakening a film structure. This can also include heat seal coatings typically applied from solution or the use of two films containing dissimilar heat seal layers. Additionally, small thermoformed cells with thin regions that rupture when squeezed can be used. Further, a reservoir 30 can have other opening means that include, but is not limited to, tear-off strips, pull tabs, and release liners.

Front Panel

Referring again to FIG. 2, the front panel 24 of applicator 10 preferably comprises a porous material, such as a fibrous non-woven, through which the product within reservoir 30 can be dispensed. Another material could include an open cell polyethylene or polyurethane foam, such as available from Sentinel Products Corporation of Hyannis, Mass. Front panel 24 is preferably substantially non-absorbent and/or preferably substantially hydrophobic when used with water based products in order to provide for residence time of the product upon the target surface. It is believed that non-absorbent fibers in a non-woven do not absorb water and swell when exposed to an aqueous based product. Exemplary non-woven fibers include polyolefins (i.e., PE and PP) and polyesters. A non-woven can be spun lace, spun bond, melt blown, carded, air laid, hydro entangled, and by other means known to one of skill in the art. Alternatively, a porous non-woven (i.e., an apertured film or web) can be used as a porous, non-absorbent material for front panel 24. Suitable materials for front panel 24 can also have sufficient strength and texture characteristics to provide a scrubbing action upon the target surface and to maintain web integrity when exposed to the material contained within reservoir 30.

In embodiments where the material within the reservoir 30 is a liquid or where the front panel 24 is exposed to liquid during use, front panel 24 preferably comprises a material that has good wet strength, durability, low product retention characteristics, and will not scratch or damage a target surface. A thermoplastic based non-woven substrate, such as PP, PE, or a polyester based non-woven substrate can meet this criteria while not absorbing a water based product. An exemplary material displaying sufficient durability and strength to a cleaning surface is a spun bond PP non-woven available from BBA Non-Wovens of Simpsonville, S.C. Other structures, such as hydroentangled materials comprising cellulose, rayon, PE and any combination thereof, can also be used. Such materials are available from Dexter Corporation of Windsor Locks, Conn. and sold under the tradename Hydraspun®. One skilled in the art will understand that a wide range of materials can be used as long as the material of interest provides the required durability to complete the particular task.

Preferably, the fiber diameter can be less than about 100 microns (100 $\mu$m), preferably less than about 50 microns (50 $\mu$m), and more preferably in the range from about 10 microns (10 $\mu$m) to about 35 microns (35 $\mu$m). A higher number of smaller diameter fibers can assist in holding onto dirt via mechanical entanglement and can also yield a softer substrate. The basis weight of the front panel 24 is preferably in the range of from about 10 g/m$^2$ to about 100 g/m$^2$, more preferably from about 15 g/m$^2$ to about 55 g/m$^2$, and most preferably from about 25 g/m$^2$ to about 45 g/m$^2$ The fibers can also be hydrophobic, oleophylic, and positively charged in order to aid in holding onto dirt, oils, and other contaminants that are desired to be removed from the target surface; preferably, an oleophylic material that facilitates the natural attachment of oils thereto. Preferably, the fibers also maintain a positive charge even when wet. A positive charge can be applied to a fiber with the treatment of a cationic polymer, such as polyacrylamide (PAM), polyethylenimine (PEI), polyvinyl pyrrolidone (PVP), polyamide epichlorohydrin (PAE). A PAE resin, produced by Hercules® under the tradename Kymene®, is one such material. It has been surprisingly found that for a glass cleaning and/or general purpose surface cleaning embodiment, PP or PE non-wovens have been found to be good materials for the application of a cleaning formula to glass and other shiny surfaces.

The applicator 10 of the present invention can be designed for use with liquid or other low viscosity products with an optional absorbent layer or material, such as tissue paper, located between reservoir 30 and front panel 24. This absorbent material can absorb and wick product, distribute product beyond the dimensions of the reservoir, and supply product to a larger surface area of front panel 24. Depending upon the viscosity of the material and the desired surface area to apply the material, absorbent layers with different capacities and wicking rates can be used to control product distribution. The basis weight of the absorbent layer can be less than about 60 g/m$^2$, preferably less than about 40 g/m$^2$, and more preferably range from at least about 10 g/m$^2$ to at least about 30 g/m$^2$. A suitable absorbent material can be a single ply of a disposable kitchen paper towel, such as Bounty®, manufactured by The Procter & Gamble Company. If reduced fluid transport is desired, higher absorbent capacity materials, such as two plies of Bounty® can be used. If celerious fluid transport is desired, less absorbent materials, such as Cellu Tissue 7020, a product of the Cellu Tissue Corporation of East Hartford, Conn., can be used as well as a creped or other corrogated material that can aid in fluid transport. However, it should be realized that one of skill in the art would understand that the absorbent material can be chosen from a wide range of absorbent materials to best meet the required capacity and wicking rate for a particular need.

Another method to control liquid flow is to use a second absorbent layer, such as a second layer of tissue, disposed between the reservoir 30 and the internal product impervious barrier layer 25. Disposing a layer in this form on both the front and back sides of the distribution portion of the reservoir 30 can help prevent product from running along the front sheet or the internal fluid impervious barrier layer 25. If this absorbent layer is only on one side of the reservoir 30, product may run along the internal fluid impervious barrier layer 25 away from the desired distribution portion of the applicator 10 prior to fluid contacting the second layer of tissue. The second layer of tissue can cover the entire surface of the applicator 10 or can cover a portion of the surface of the applicator 10 from the outlet of the reservoir 30 to a region where the transport of fluid is desired. For example, a two- to six-inch (5.08 cm–15.24 cm) strip of tissue can comprise the second layer located between the fluid impervious barrier layer 25 and the reservoir 30 and located from the top of the applicator 10 to a region slightly below the outlet of reservoir 30.

In addition, an SMS-type structure (spun-bond/melt-blown/spun-bond) provided by the BBA Non-wovens, Inc., Simpsonville, N.C., can be used as would be known to one of the skill in the art. This structure incorporates a melt-blown layer that can help transport fluid across front panel 24.

Referring again to FIG. 2, the applicator 10 of the present invention can include a barrier layer 25 that defines the front inner surface 32 that faces the wearer's hand during use. This can protect the user's hand from contact with the material during the dispensing and/or dispersing operation. Preferably, the barrier layer 25 is preferably impervious to the material contained within reservoir 30. Suitable barrier materials can include polymer films, such as PE, PP, EVA, and polymer blends or co-extrusions, which can be rendered extensible by methods described below. Materials that are embossed, whether or not rendered extensible, can provide improved tactile properties and greater control over the applicator 10 in terms of contact and coefficient of friction with the hand. Preferably, the material in the surface alteration is made such that the coefficient of friction between the inner surface 32 and the wearer's hand is greater than the coefficient of friction between the outer surface 33 and the target surface. It is believed that this can reduce the likelihood that the applicator 10 can slip or rotate inadvertently in use. The barrier layer 25 can also be combined with another "softness enhancing" material that provides additional comfort, softness, and tactile feel to a user's hand on the front inner surface 32. Such materials can include, but are not limited to, fibrous (i.e., natural, synthetic, and/or combinations thereof) and/or foamed materials.

Applicators 10, such as mitts, can be designed to deliver products to one or both surfaces. Applicator 10 can also be used independently with a product applied via another source to accomplish dispersion of the product and, if desired, removal of the product from a surface by absorption. As would be known to one of skill in the art, applicators 10 can be designed to direct a material towards the opposite surface of the applicator 10 after inversion. For example, if the applicator 10 is used for one function, it can then be turned inside out and activated again to deliver fresh product from the former internal surface.

As material is released, it can be desirable for a user to be able to identify when the preferred amount of material has been released onto the front panel 24 of applicator 10. This can be accomplished by incorporating a marking on the substrates to identify the surface area that would be covered by the preferred amount of dispensed material. This marking can be in the form of an ink mark, embossed pattern, or any other means of visual identification on any or all layers of the substrates, as would be known to one of skill in the art. The shape and size of a marking could be varied and based on the size and shape assumed by the preferred amount of material when dispensed within the particular embodiment of the applicator 10. For example, the use of different glue patterns that promote faster wicking of the material in a particular direction could require that the shape be a large elliptical pattern.

In some embodiments, the reservoir 30 is able to rupture at a relatively low force. This force can be in the range from at least about 1 lb. (4.448N) to at least about 3 lbs. (13.39N), when the consumer is ready to use the applicator 10. However, the reservoir 30 should be capable of surviving relatively higher forces, such as in the range from at least about 10 lbs. (44.48N) to at least about 40 lbs. (177.9N) when the applicator 10 is in retail distribution channels. Such higher forces can be accomplished by folding the reservoir 30 on the frangible seal or between the frangible seal and the reservoir 30. In a particular embodiment, folding the reservoir has been shown to effectively raise the bursting force from at least about 30 lbs. (133.4N) to at least about 40 lbs. (177.9N). Additionally, the applicator 10 can be bi- or tri-folded, or otherwise folded in order to provide extra protection to the seal.

Figure 8:
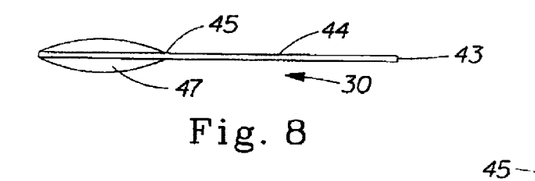
FIG. 8 is an elevational view of the rupturable reservoir of FIG. 7.
Figure 9:
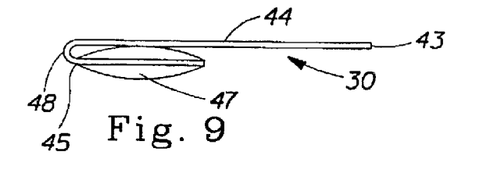
FIG. 9 is an elevational view of the rupturable reservoir of FIG. 8 folded in the vicinity of the rupturable seal.

FIG. 8 provides an elevational view of an exemplary reservoir 30 and illustrates the use of folding techniques to protect a frangible seal from premature rupture. As shown in FIG. 9, reservoir 30 has been folded at location 48 adjacent to a rupturable seal 45. Folding the reservoir 30 can crimp or pinch off the fluid pathway and provide reservoir 30 with the capability to withstand significantly more internal pressure without leakage than would normally be possible for a rupturable seal 45.

Figure 10:
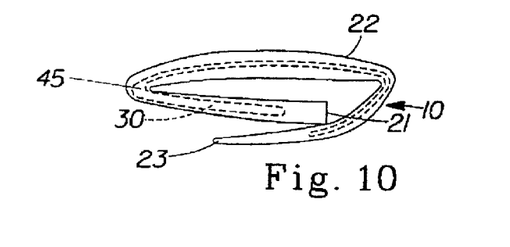
FIG. 10 is an elevational view of the applicator of FIG. 3 folded in the vicinity of the rupturable seal; and, FIG. 11 is a cross-sectional view of another exemplary applicator embodiment.

FIG. 10 depicts an exemplary tri-folding of an applicator 10 to isolate reservoir 30. As shown, the additional fold in the vicinity of the distal end of the reservoir 30 can provide additional security against premature dispensing by isolating fluid outlets from the remainder of the reservoir 30. A bi-fold, tri-fold, "Z"-fold, or any mechanism as would be known to one of skill in the art can provide enhanced resistance to premature activation.

Back Panel

Referring again to FIG. 2, the optional back panel 26 can aid in keeping the applicator 10 on the user. When applicator 10 is a semi-enclosed applicator, the back panel 26 can enclose the hand of a user and remove product applied to a surface via the front panel 24. The back panel 26 can be constructed of materials, including, but not limited to, thermoplastic films, non-wovens, scrims, and/or papers.

After the product has been dispensed and dispersed onto a target surface, it may be desirable to absorb and/or remove excess product, contaminants, and/or particles from the target surface while minimizing filming, streaking, and/or residual matter. Accordingly, the back panel 26 of the applicator 10 can be made from a material that is substantially absorbent. By way of example, the back panel 26 can be constructed of absorbent fibers that swell when exposed to the product. Exemplary absorbent fibers include man-made fibers dried from cellulose (i.e., rayon, cellulose acetate, and cellulose triacetate) and natural cellulose fibers. Exemplary absorbent materials can also include particles and fibers made from super-absorbent polymers (i.e., cross-linked copolymers of acrylic acid) that are incorporated into the back panel 26.

Back panel 26 can be constructed from non-woven materials, apertured films, absorbent or fibrous absorbent materials, super-absorbent polymer fibers or powders, laminates, and/or combinations thereof. Absorbent non-wovens can be made by methods discussed supra. Preferably, the back panel 26 material preferably has sufficient capacity to absorb at least about four or more times its own weight of a liquid product. For liquids, four plies of disposable kitchen paper towels, such as BOUNTY®, a product of The Procter & Gamble Company, has been found suitable. This paper towel material typically has the capacity to absorb between at least about eight and at least about nine times its own weight in water and can naturally retain a liquid more than a thermoplastic non-woven material without over-saturation or substantial loss of web integrity. The fibers in the absorbent paper towel material can absorb a product and swell to some extent during absorption. If high wet strength is desired, other structures, such as hydro entangled materials comprising cellulose, rayon, and PE, can provide enhanced strength. Further, absorbent foams, such as those described in U.S. Pat. No. 5,571,849 may also be suitable for use as the back panel 26.

In a preferred embodiment, the absorbent layer would have a range of at least about two to at least about eight times, and more preferably from at least about three to at least about five times the absorbent capacity of the volume of product within reservoir 30. Without desiring to be bound by theory, it is believed that extra absorbency can further aid in producing a streak-free shine to a glass panel or other surface because back panel 26 can remove nearly all product on the target surface without leaving a film or streak of cleaning solution. Additionally, as would be known to one of skill in the art, certain materials can have a relatively higher capillary action in order to remove product from the surface of back panel 26 and can thus require less absorbent capacity as compared to reservoir 30 capacity.

It has been found that the structure described in DesMarais, U.S. Pat. No. 5,571,849 is suitable for use as or in back panel 26. Further, additional additives, such as wet strength additives, dry strength additives, cationic treatments, cationic promoters, softeners, and absorbency aids, can be used.

As discussed supra, one side of applicator 10 can be designed with a majority of non-absorbent fibers (i.e., substantially non-absorbent) and the other side can be designed with a majority of absorbent fibers (i.e., substantially absorbent). However, depending upon the specific application, the material, the environmental conditions, and the benefit sought, the amount of product that the substantially absorbent side absorbs and the amount of product the substantially non-absorbent side absorbs may not be constant. Without desiring to be bound by theory, it is believed that the substantially absorbent side can have a relatively higher absorbent capacity than the substantially non-absorbent side for a particular material. The ratio of the absorbent capacity of the substantially absorbent side to the absorbent capacity of the substantially non-absorbent side is preferably greater than at least about one, preferably greater than at least about two, and more preferably greater than at least about four.

In another embodiment, applicator 10 is provided with multiple layers on either the front panel 24 or the back panel 26 in order to provide additional absorbency and/or cleaning surfaces. Preferably, these additional layers are heat sealed only to the perimeter of applicator 10 and sealed in such a way that the layer becomes peelable. However, layers can be attached and removed by other methods, including, but not limited to, preferations and peelable adhesives. The layers can be slightly offset at the cuff region 21 or an additional material, such as a tab, can protrude from the layer to facilitate removal. Peelable heat seals can be provided by heat sealing the individual layers at a lower temperature or with less seal time. Layers can also be made peelable by using a contamination layer or any other method known to one of skill in the art. By way of example, on a heavily soiled surface, the front panel 24 and/or back panel 26 can become soiled to an undesirable level prior to all product in reservoir 30 being used. An extra layer or layers of a PP non-woven could be used on the front panel 24 to allow a user to peel off a dirty layer as required. This can also provide continued use of the applicator 10 on additional surfaces if additional product remains in the reservoir 30. Similarly, the back panel 26 can be supplied with multiple layers of an absorbent paper towel, such as BOUNTY®, made by The Procter & Gamble Company. These absorbent backside layers can be coated with a thin barrier material, such as PE, that can prevent fluid from saturating layers that are not in use. When this outer layer becomes soiled, the outer layer can then be removed to expose a new, clean layer.

Referring again to FIG. 2, back panel 26 can also comprise an optional additional fluid impervious barrier layer 27 to protect a wearer's hand from contact with products absorbed by the back panel 26. The interior portion of impervious barrier layer 27 can define the back inner surface 34 facing the wearer's hand during use. This optional additional fluid impervious barrier layer 27 can be similar in construction and materials as barrier layer 25 described supra. In particular, when a second barrier layer 27 is employed, it may be desirable for some applications to include an optional secondary product reservoir 35 to deliver a second possibly diverse composition to the target surface. For example, water or a neutralizing agent placed in the secondary fluid reservoir 35 could be used after the product in reservoir 30 has been depleted.

Product

To facilitate spreading or dispersal of the product upon a target surface, particularly to counteract the tendency of the product to remain in a localized distribution pattern, it is preferred to utilize products that are tailored to be wettable upon the target surface or the front panel 24 of applicator 10. Other factors that can aid in dispersion or distribution of the product upon the target surface can include the use of substances that exhibit a thixotropic behavior. Lateral mechanical spreading actions can also provide additional interaction with the product for thixotropic substances and can provide additional benefits, such as lathering, foam generation, scrubbing, abrasion, and combinations thereof.

Successful dispersion occurs when a portion of the deposited or dispensed product subsequently coats a portion of the target surface where the product was not originally deposited. Upon removal of the applicator 10 from the target surface, at least some of the product should remain located on the target surface, preferably in a substantially uniform pattern.

Applicator

The applicator 10 of the present invention can be packaged in any suitable fashion. However, a preferred method of packaging the applicator 10 involves tri-folding an applicator 10 into a "C"-folded configuration. A plurality of folded applicators 10 can then be placed within an outer carton or wrapper. It is believed that a cushioning effect of the superposed folded portion of the applicators 10 can provide additional protection against premature rupture of the reservoir 30.

It is also believed that the applicator 10 of the present invention can also allow a user to clean a target surface without the problems associated with conventional spray-and-wipe products. One problem queried is the potential contact irritation and/or inhalation of potentially volatile chemicals. Additionally, applying a product directly on a target surface means greater efficiency in product use and avoiding product contacting surfaces that are adjacent to a target surface that may be sensitive to the material in use. In particular, the applicators 10 can eliminate or reduce performance and surface safety issues that can result from material run-off. Further, multiple products are not required for a cleaning task.

The applicators 10 of the present invention can have multiple methods of use. A user can remove an applicator 10 from a container, unfold the applicator 10, and fit a hand into or place a hand on the backside of applicator 10. The reservoir 30 can then be activated to release the product. Activation can be by any suitable method, such as pressing on the reservoir 30 with one or more fingers, with the palm of a free hand, or by pressing the reservoir 30 against a solid surface. The amount of product dosed can be controlled by instructing a user to press the reservoir 30 to release an amount of product for the use intended. These parameters can be printed instructions for use or written or graphically illustrated directly on the front panel 24 of the applicator 10. In a preferred embodiment, instructions for use can call for the release of product to wick an area that is demarcated around the orifice from which the product is dispersed. The area to be wicked can be shown by means of any graphical representation or in words. In a preferred embodiment, the area to be wicked can be shown via a circle or other geometric figure. The size of the geometric figure can reflect the optimum composition volume of product for the task and can be a function of the substrate raw material, wicking ability, and/or basis weight of the material comprising applicator 10. In most cases, the geometric figure can be a circle having a diameter ranging from about 1 cm to about 15 cm, and more preferably from about 2 cm to about 8 cm. One of skill in the art will also recognize that the applicator 10 can be designed so that product preferentially wicks in one direction versus another. In such instances, a graphical demarcation on the applicator 10 can preferably consist of one or more non-circular geometric figures.

However, it should also be realized that an applicator 10 can be used without the benefit of the reservoir 30. Thus, a two-sided applicator 10 can be used together with a conventional spray bottle. While this may not be a preferred method of use, some of the benefits arising from the choice of absorbent and non-absorbent substrates can remain as well as a convenient mitt form for better retention on a hand. Accordingly, the methods for use can be similar to those described above, wherein the preferred dosing mechanism from the reservoir 30 with an equivalent or slightly larger volume (e.g., about 1.0 to about 1.5 times of material delivered from a spray bottle).

At the end of its use, the applicator 10 can be everted by making a fist with the mitt hand and pulling the structure over the fist from the cuff region 21 of the applicator 10. In this way, the layers are transposed and the inner surface of the front panel 24 and the inner surface of the back panel 26 become the outer surfaces of the waste article.

Exemplary Embodiment I

An applicator made in accordance with the present invention may include a glass cleaning semi-enclosed mitt that provides a flexible structure for distributing a glass cleaning substance onto a target glass surface. This applicator would include a first fluid material reservoir containing from about 5 $cm^3$ to about 20 $cm^3$ of a liquid cleaning product, such as CINCH®, a brand available from The Procter & Gamble Company, Cincinnati, Ohio. The applicator may also include a front panel layer comprising a polypropylene spun bonded non-woven material to provide a substrate for spreading a cleaning material and for scrubbing the surface with the cleaning material. An exemplary spun bonded non-woven would have a basis weight in the range from about 10 gsm to about 100 gsm, more preferably from about 15 gsm to about 55 gsm, and most preferably from about 25 gsm to about 45 gsm. An exemplary spun bonded non-woven is commercially available from BBA Non-Woven, Inc., Simpsonville, S.C., under the name Celestra®. In addition, the material would preferably be substantially free of surfactants or other treatments that could leave residual material on the surface being cleaned.

A flexible film reservoir 30 comprising at least one co-extruded film could be supplied with a frangible seal connected to a distribution channel that provides fluid communication with one or more distribution apertures located in a region or application surface of the applicator corresponding to the position of a user's fingers during use. The reservoir kit could be positioned in the applicator near the cuff region so that the frangible seal is located below the palm of the wearer's hand.

The reservoir in the distribution channel could be located between a layer of absorbent material (i.e., a tissue layer) and a barrier layer (i.e., a barrier film layer). The absorbent layer can wick and assist in spreading the material throughout the surface of the applicator during use while the barrier layer keeps the material from contacting the user. The tissue layer can have a basis weight in the range from about 10 gsm to about 30 gsm, most preferably about 20 gsm. An exemplary tissue layer could be a single ply of CelluTissue 7020 manufactured by The CelluTissue Corporation, East Hartford, Conn. In the alternative, tissue layer can include a single ply of BOUNTY®, one tissue available from The Procter & Gamble Company, Cincinnati, Ohio. An additional absorbent layer (i.e., another tissue layer), which can be similar in material and construction to the first tissue layer, could also be located between the barrier film layer in the reservoir and/or the distribution channel to direct the material towards a localized region of the applicator. A pressure sensitive adhesive, such as H2031, manufactured by The ATO Findlay Company, Wauwatosa, Wis., can provide adhesion required to combine the layers of the present applicator. An adhesive can be applied as lines with the spacing of about 3 mm to about 4 mm apart at a basis weight of about 5 gsm. The back panel of the applicator can comprise a substantially absorbent material, such as a multiple ply layer (e.g., four plies) of BOUNTY® paper towel product. A multiple ply layer of substantially absorbent material can be used to provide a distinct surface to remove and absorb residual glass cleaning product and/or dirt left on the glass after cleaning with the non-woven side of the applicator. Friction enhancing elements can be located on the inner surface of the front panel or the back panel of the applicator. In another embodiment, the friction enhancing elements can comprise non-slip material coatings, such as the 195-338 hot melt manufactured by The ATO Findlay Company, Wauwatosa, Wis. Friction enhancing strips can be positioned in the top half of the applicator to provide contact with the fingers and/or palm of the user's hand and prevent the applicator from slipping on the user's hand. Friction enhancing elements preferably have a basis weight ranging from about 40 gsm to about 180 gsm, and more preferably from about 90 gsm to about 130 gsm.

The applicator of the present example can be used for cleaning glass surfaces, including, but not limited to, inside and outside windows, mirrors, television screens, tables, and car windows. This applicator can also be used to clean other surfaces, such as vinyl, Formica®, enamels, porcelain, wood, aluminum, steel, chrome, and the like. Applications include cleaning or refreshing countertops, indoor furniture, outdoor furniture, upholstery, painted walls, wallpapers, and floors.

Exemplary Embodiment II

Figure 11:
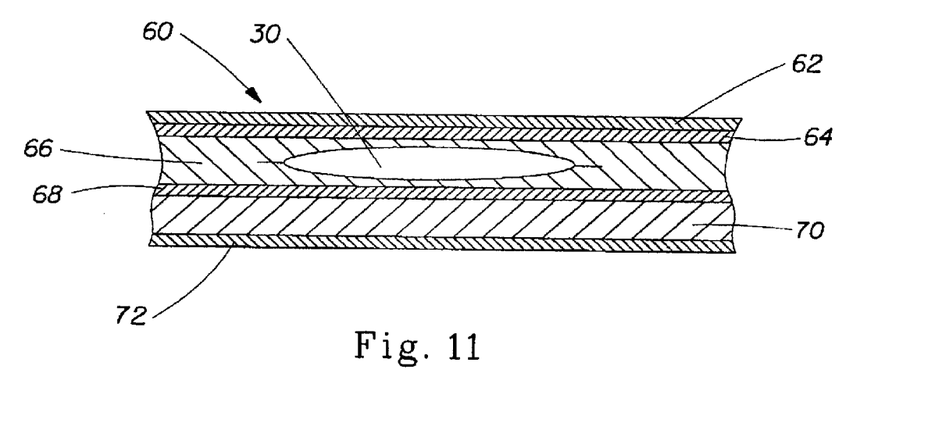

As shown in FIG. 11, a lotion applicator 60 can be constructed with a LLDPE non-woven as an exemplary first side, or skin application side 62 followed by a membrane 64 that is capable of metering and/or dosing a product from a rupturable reservoir 30. The non-woven and membrane can be sealed to an exemplary second side, or barrier layer 68, such as a polyolefin film that is about 1 mil to about 2 mils thick; for example, LDPE, and form internal cavity 66 therebetween. An additional layer 70, such as a foam, embossed polyethylene film, and/or polyester batting, can be used to provide thickness so that the applicator feels comfortable to the hand, conforms to the surface being treated, and is easier to hold. An additional layer 72, such as a friction enhancing coating, or a body adhesive, can be added to help a user hold the pad while cleaning. This can be accomplished with an adhesive similar to those used in bandages incorporating a hydrogel or with a form film technology, as disclosed in U.S. Pat. No. 5,662,758. The applicator 60 should be sealed or adhesively bonded around its perimeter to prevent the substance contained in reservoir 30 from being transported to side 62 of applicator 60 upon the dispensing of the substance from reservoir 30. Such sealing or bonding thus can aid in preventing contact of the substance 3 with the skin of a user.

Specifically, side 62 is formed from a 60 gsm LLDPE non-woven, available from BBA Non-wovens, Inc, Simpsonville, S.C. The membrane 64 is a 100-mesh hydroapertured film available from Tredegar, Terre Haute, Ind. A pouch containing 10 $cm^3$ of substance is made from a Surlyn®/PE co-extruded film that is laminated to a metallized PET layer structure with at least one side of the pouch having a frangible seal. For example, the pouch may contain a skin care lotion. The preferred film for barrier layer 68 is a 1 mil (0.025 mm) LDPE film available from Clopay, Mason, Ohio and layer 70 is a 0.2 cm to 0.4 cm thick cellulose-based thermally bonded air-laid structure from Concert Industries, Vancouver, BC. A peelable body adhesive is optionally coated on the surface of the foam.

Thus, the user would lay his palm on the pad so that the peelable body adhesive remains in contact and attached to the user's palm. The user would then make a fist causing the pouch to rupture. The product in the pouch would then be released into the cavity. The user then applies the lotion or product to the body by wiping or rubbing the pad with the outer surface in contact with the skin. The membrane then meters the product so that a thin film is deposited on the skin as the pad is wiped across the surface.

While particular embodiments of the present invention have been illustrated and described, it would be obvious to those skilled in the art that various other changes and modifications can be made without departing from the spirit and scope of the invention. Any of the aspects of the invention of the present invention found to offer advantages over the state of the art may be used separately or in any suitable combination to achieve some or all of the benefits of the invention disclosed herein.

What is claimed is:

1. An applicator for distributing a product onto a target surface, said applicator having a first side, a second side, and an internal cavity disposed between said first and second sides, said applicator further comprising:
   (a) at least one substantially fluid-impervious barrier layer disposed within said internal cavity adjacent at least one of said sides; and
   (b) a first rupturable, product-containing, non-laminated flexible film reservoir comprising at least one co-extruded film disposed adjacent to said barrier layer; and,
       wherein said product is released from said reservoir through said applicator to said target surface in response to an application of pressure to said reservoir.

2. The applicator of claim 1, wherein said product is dispensed from said reservoir through a fluid pathway, said fluid pathway being normally closed, except when said product dispensing is desired.

3. The applicator of claim 1, wherein said first side comprises a first material, said first material being at least partially absorbent of said product from said rupturable reservoir to facilitate removal thereof from said target surface, and said second side comprises a second material, said second material being selected to facilitate dispensing of said product from said rupturable reservoir and application of said product to said target surface.

4. The applicator of claim 1, further comprising a structure to temporarily increase the resistance of said reservoir to rupture.

5. The applicator of claim 1, further comprising a dispensing aperture disposed proximate to said rupturable reservoir.

6. The applicator of claim 1, further comprising a friction-enhancing element disposed upon said second side.

7. The applicator of claim 1, further comprising a layer of wicking material located adjacent at least one of said first and second sides, said wicking material including wicking properties with respect to said product contained in said rupturable reservoir.

8. The applicator of claim 1, wherein said applicator is provided in the form of a mitt to be used on at least of a portion of the hand of a user.

9. The applicator of claim 1, wherein said first side is absorbent.

10. The applicator of claim 9, wherein said second side is non-absorbent.

11. The applicator of claim 10, wherein said first side comprises a fibrous material.

12. The applicator of claim 10 wherein said second side comprises a fibrous material.

13. The applicator of claim 12, wherein said fibrous material has a diameter less than about 100 $\mu$m.

14. The applicator of claim 1, wherein said reservoir further comprises at least one frangible seal having a resistance to bursting.

15. The applicator of claim 14, further comprising at least one foldable portion located adjacent said at least one frangible seal, and wherein said applicator has a folded condition in which said foldable portion is folded and the resistance to bursting forces of said at least one frangible seal is increased.

16. The applicator of claim 1, further comprising a second fluid-containing reservoir in selective fluid communication with one of said first or second sides.

17. A method for forming an applicator for distributing a substance onto a target surface, wherein said applicator has a first side, a second side, an internal cavity disposed between said first and second sides, at least one substantially fluid-impervious barrier layer disposed within said internal cavity adjacent at least one of said sides, a first product-containing flexible film reservoir comprising at least one non-laminated co-extruded film disposed adjacent said barrier layer, and a dispensing aperture associated with said reservoir through which said product is selectively distributed to one of said first and second sides, said method comprising the steps of:
   (a) providing a first web corresponding to one of said first and second sides;
   (b) providing a second web corresponding to the other of said first and second sides;
   (c) providing first product-containing reservoir in a predetermined location in relation to said first and second webs;
   (d) securing said reservoir relative to said first and second webs and attaching said first and second webs to one another in such a way as to form an internal cavity therebetween; and,
   (e) cutting said applicator in a desired outline shape from said attached first and second webs to define said applicator.

18. An applicator for distributing a product onto a target surface, said applicator comprising:
   (a) a first layer having a first face;
   (b) a second permeable layer having a first face;
       wherein said first face of said first layer and said first face of said second permeable layer are in a face-to-face relationship; and,
   (c) a product-containing non-laminated co-extruded film reservoir disposed adjacent either of said first layer or said second permeable layer; and,
       wherein said product is released to said target surface upon application of pressure to said reservoir.

19. The applicator of claim 18 wherein said reservoir further comprises a predetermined weak region for releasing said product from said reservoir to said target surface.

* * * * *